United States Patent
Lundström

(10) Patent No.: US 12,310,775 B2
(45) Date of Patent: May 27, 2025

(54) X-RAY SYSTEM

(71) Applicant: Excillum AB, Kista (SE)

(72) Inventor: Ulf Lundström, Kista (SE)

(73) Assignee: Excillum AB, Kista (SE)

( * ) Notice: Subject to any disclaimer, the term of this patent is extended or adjusted under 35 U.S.C. 154(b) by 266 days.

(21) Appl. No.: 18/249,442

(22) PCT Filed: Oct. 18, 2021

(86) PCT No.: PCT/EP2021/078778
§ 371 (c)(1),
(2) Date: Apr. 18, 2023

(87) PCT Pub. No.: WO2022/084234
PCT Pub. Date: Apr. 28, 2022

(65) Prior Publication Data
US 2023/0380786 A1    Nov. 30, 2023

(30) Foreign Application Priority Data
Oct. 19, 2020   (EP) ...................... 20202574

(51) Int. Cl.
*A61B 6/00*   (2024.01)
*A61B 6/06*   (2006.01)
(Continued)

(52) U.S. Cl.
CPC ............. *A61B 6/482* (2013.01); *A61B 6/06* (2013.01); *A61B 6/107* (2013.01); *A61B 6/40* (2013.01)

(58) Field of Classification Search
CPC .. A61B 6/06; A61B 6/107; A61B 6/40; A61B 6/482; G01T 1/00; H05G 1/02
See application file for complete search history.

(56) References Cited

U.S. PATENT DOCUMENTS

2017/0160212 A1*  6/2017  Kleine ................... G01T 7/005

FOREIGN PATENT DOCUMENTS

| EP | 1462794 A2 | 9/2004 |
| EP | 1462794 A3 | 4/2006 |

OTHER PUBLICATIONS

International Preliminary Report on Patentability (PCT/IPEA/409) issued in corresponding International Patent Application No. PCT/EP2021/078778 dated Sep. 29, 2022. (14 pages).
(Continued)

*Primary Examiner* — Dani Fox
(74) *Attorney, Agent, or Firm* — Buchanan Ingersoll & Rooney PC

(57) ABSTRACT

An X-ray system is disclosed, including an electron-impact X-ray source configured to generate an X-ray beam; a radiation-shielded housing having an X-ray outlet port; an X-ray optical element arranged within the radiation-shielded housing configured to direct the X-ray beam toward the outlet port; a shutter arranged at the outlet port, the shutter being movable between an open position at which X-ray output through the outlet port is allowed, and a closed position at which X-ray output through the outlet port is prevented; and a detector arranged to detect X-ray radiation from the X-ray source directed towards the outlet port, wherein the detector is configured to detect X-ray radiation within a first energy range. A corresponding method of operating an X-ray system is also disclosed.

15 Claims, 3 Drawing Sheets

(51) Int. Cl.
    *A61B 6/10*      (2006.01)
    *A61B 6/40*      (2024.01)

(56)            References Cited

OTHER PUBLICATIONS

International Search Report (PCT/ISA/210) and Written Opinion (PCT/ISA/237) mailed on Feb. 11, 2022 by the European Patent Office as the International Searching Authority for International Application No. PCT/EP2021/078778. (12 pages).

* cited by examiner

X-RAY SYSTEM

TECHNICAL FIELD

The present invention relates generally to X-ray systems.

BACKGROUND

An X-ray system typically comprises an X-ray source and X-ray optics positioned to collect and direct X-ray radiation generated by the X-ray source. The amount of useful X-ray radiation that can be made available from an X-ray system is thus partly determined by the amount of radiation that can be collected by the optics. The prior art is limited in this regard by overall safety requirements and geometrical constraints that restrict how much of the generated radiation that can be collected and made useful as an output from the X-ray system.

SUMMARY

A typical prior art X-ray system comprises an X-ray source with a shutter, and an X-ray optical element to collect generated X-ray radiation and provide useful output. As will be appreciated, more useful X-ray radiation can be made available if the X-ray optics is positioned closer to the X-ray source. However, in the prior art, the minimum distance between the source and the optics is determined by the internal geometry of the source and the dimensions of the shutter.

The shutter is required for safety reasons; it must be possible to protect the surroundings, in particular humans, from unintended exposure to X-rays at all times. If the X-ray optics is not properly adjusted when the source is turned on radiation could potentially end up almost anywhere. In the prior art, X-ray optics is therefore arranged downstream from the shutter, which puts a restraint on how short the distance between the source and the optics can become and thus also on how much useful X-ray radiation can be made available.

The present invention provides for a safe way to put the optics closer to the source by providing a radiation-shielded housing, preferably with only one intended X-ray outlet. The housing may be an extension of the X-ray source enclosure or it may be connected to the enclosure either rigidly or flexibly. It is even conceivable that the source and the housing are disconnected from each other, provided that a radiation trap is present where they meet to prevent any leakage of X-ray radiation. The present invention is particularly useful in electron-impact X-ray systems, in which X-ray radiation is generated by interaction between an electron beam and a target. The target may be a solid target, such as a reflection target or a transmission target, or a liquid target, such as a liquid jet target.

A general idea forming a basis for the present invention is that the X-ray optical element(s) can be placed closer to the X-ray source if disposed within such radiation-shielded housing and thus upstream of the shutter, wherein the shutter that prevents inadvertent output of X-ray radiation is disposed at an outlet port of the radiation-shielded housing. The X-ray optics is configured to direct X-ray radiation generated by the X-ray source toward the outlet port. The radiation-shielded housing thus serves the purpose of preventing leakage of X-ray radiation and only allow output through the outlet port, and the shutter is used for controlling whether output through the outlet port is allowed or prevented.

Traditionally, the safety shutter has been integrated with, i.e. built into, the X-ray source and X-ray optics and/or monochromators have been arranged downstream from the safety shutter. Hence, it may appear counter-intuitive to the skilled person to instead move the safety shutter to a position downstream from the optics/monochromators. In accordance with the present invention, however, this is made possible by virtue of the radiation-shielded housing, inside which the X-ray optical element is placed.

Conveniently, there may be provided one or more detectors inside the radiation-shielded housing to detect X-ray radiation that is directed towards the outlet port. For example, a detector may be attached to the shutter on the side thereof facing the interior of the radiation-shielded housing. Such a detector may preferably be embodied as one or more diodes. Alternative detectors may comprise pixelated detectors, providing more information during alignment, or scintillator-based detectors that may provide better sensitivity. Embodiments comprise detectors configured to detect X-ray radiation within a first energy range. The energy range may have an upper limit, a lower limit, or both an upper and a lower limit. In an exemplary embodiment a filter is arranged to prevent X-ray radiation of energy outside of said first energy range from reaching the detector. Other embodiments may comprise separate detection of X-ray radiation from at least a first and a second energy range. In particular, separate detection of X-ray photons having an energy within a desired energy range and X-ray photons with an energy that is above said desired energy range may be advantageous. A first signal generated by photons within a desired energy range may be used during an alignment procedure. Alignment between the X-ray source and the X-ray optical element and/or between the X-ray optical element and the outlet port may be adjusted to increase this signal. A second signal generated by photons with an energy above said desired energy range may be used to mitigate malfunction as described below.

Inclusion of a detector configured to detect X-ray radiation within a certain energy range directed towards the outlet port is advantageous in that it may be used as an alignment tool making the adjustments of position and/or orientation of the X-ray optical element easier to perform for an operator or possible to automatize. Furthermore, such a detector together with the shutter placed at the outlet port may also be used to prevent X-ray radiation with an energy outside of a desired energy range from being emitted through the outlet port. These and other advantages are further described below in various exemplary embodiments.

Typically, an X-ray system is designed to deliver X-ray radiation within a predetermined photon energy range, and monochromizing X-ray optics is regularly used for this purpose. In case of malfunction, however, such as de-alignment of components in the X-ray system, X-ray radiation having a photon energy outside of the predetermined range may pass the optics. In some embodiments, such situation is addressed by configuring the detector to separately detect photons having an energy outside, e.g. above, the predetermined energy range. If it is detected that an amount of photons having an energy outside of the predetermined energy range exceeds a predetermined threshold, then the system may be configured to ensure that the shutter is in a closed position to prevent output of any X-ray radiation of such energies through the outlet port. Movement of the shutter between the closed position and the open position is preferably effected using an electro-mechanical actuator, a motor or the like.

The X-ray system may also be provided with an outer radiation shield, or cabinet, configured to block radiation. The cabinet may enclose at least some of the X-ray source, the X-ray optics, a sample position, and a detection device. For example, such outer cabinet may be configured to block radiation at photon energies corresponding to those energies that the X-ray optics is designed to provide as an output. In some implementations, the detector may therefore be configured to detect radiation that may risk passing through the outer cabinet, while being non-sensitive to radiation corresponding to the intended output. In this manner X-ray radiation of a higher energy than the predetermined energy range, which might otherwise inadvertently be emitted and possibly transmitted through the outer radiation shield, may be detected and confined to the inner radiation shielding by ensuring that shutter is closed if such X-ray radiation is detected.

The provision of a detector for detecting X-ray radiation directed towards the outlet port can also be used for alignment of components of the X-ray system. By detecting X-ray radiation directed towards the outlet port, for example radiation within the predetermined range, and by feeding a detector signal from the detector to a controller, an alignment between the X-ray source and the X-ray optics and/or between the X-ray optics and the outlet port can be adjusted by the controller such that the detector signal is increased. To this end, the controller is preferably coupled to manipulators that can be used for moving an X-ray spot of the X-ray source and/or the position or orientation of the X-ray optics. Conveniently, such alignment can be performed while the shutter is in its closed position and thus preventing any X-ray radiation from being output through the outlet port. A manipulator arranged to adjust the position and/or orientation of the X-ray optical element is thus preferably controllable from the outside of the radiation shielded housing. This is advantageous in that poor alignment may cause X-ray radiation with an energy outside the predetermined range to reach the outlet port.

Movement of the X-ray spot with respect to the X-ray optics may e.g. be accomplished by movement of the entire X-ray source, by deflecting an electron beam impacting a target for generating X-ray radiation over said target, or by moving an X-ray target. Different modes of translation may be used in different directions, e.g. movement of the X-ray spot in a first direction may be realized by deflecting the electron beam whereas movement along another direction, such as perpendicular to the first direction may be realized by moving the target.

Movement of the X-ray optics may e.g. be accomplished with the aid of motors, such as stepper motors, or actuators, such as electromagnetic or piezoelectric actuators.

Several modifications and variations are possible within the scope of the invention. In particular, X-ray sources comprising a multi-material target, more than one target, or more than one electron beam are conceivable within the scope of the present inventive concept. Also X-ray optics designed to direct X-ray radiation of more than one well-defined wavelength are contemplated. Furthermore, X-ray systems of the type described herein may advantageously be tailored to specific applications exemplified by but not limited to medical diagnosis, non-destructive testing, lithography, crystal analysis, microscopy, materials science, microscopy surface physics, protein structure determination by X-ray diffraction, X-ray photo spectroscopy (XPS), critical dimension small angle X-ray scattering (CD-SAXS), and X-ray fluorescence (XRF).

BRIEF DESCRIPTION OF THE DRAWINGS

In the following detailed description, reference is made to the accompanying drawings, on which.

DETAILED DESCRIPTION

Figure 1:
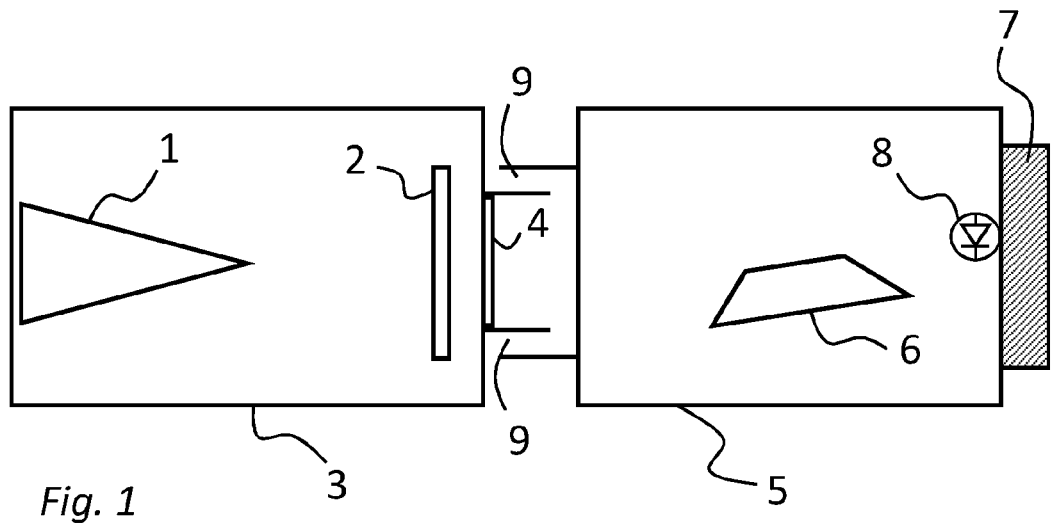
FIG. 1 schematically shows an example of an X-ray system.

FIG. 1 shows schematically an example of an X-ray system. The X-ray system is provided with an enclosure 3 from which X-ray radiation is emitted through an X-ray transparent window 4. X-ray radiation is generated by electrons emitted from an electron source 1 and impacting on a target 2 at an interaction region, thus creating an X-ray spot. A radiation-shielded housing 5 is arranged adjacent to the enclosure 3 and receives X-ray radiation emitted through the window 4. X-ray optics 6 is provided within the radiation-shielded housing 5. The housing 5 and the enclosure 3 are, in this example, independently movable with respect to each other. Thus, alignment may be performed by moving either the housing 5 or the enclosure 3 or both. To prevent radiation leakage, a radiation trap 9 may be arranged at an interface between the housing 5 and the enclosure 3. The housing 5 is provided with an outlet port, through which X-ray radiation can be output. In order to prevent inadvertent output of X-ray radiation, the outlet port is provided with a shutter 7 that is movable between an open position at which X-ray output through the outlet port is allowed, and a closed position at which X-ray output through the outlet port is prevented. When the shutter 7 is closed, no X-ray radiation is emitted to the surrounding environment. When the shutter 7 is open, X-ray radiation can be emitted through the outlet port in the housing otherwise covered by the shutter. One or more detectors (indicated at reference numeral 8 in FIG. 1) may be provided, for example on the shutter 7, to detect any X-ray radiation directed towards the outlet port. Hence, when the shutter 7 is closed, the detector(s) 8 provides a signal indicative of the amount of X-ray radiation reaching the shutter. During an alignment procedure, the relative position of the X-ray optics and the X-ray spot may be adjusted such that this signal increases.

It is also conceivable to perform an alignment procedure based on feedback from a detector located at a sample position (i.e. at a position where a sample under study is to be placed) or in the beam path upstream or downstream from the sample position. The shutter 7 will then be in its open position during the alignment procedure in order for X-ray radiation to reach the detector.

The X-ray optical element 6 can be a mirror, such as a multilayer mirror; a zone plate; a monocapillary optical element; or a polycapillary optical element. In some preferred embodiments, the X-ray optical element is a Montel mirror. In other embodiments, the X-ray optical element may be implemented as crystal optics, e.g. doubly curved crystal optics (DCC optics).

The inside of the radiation-shielded housing 5 may be at a reduced pressure, or it may be filled with an inert gas such as helium or nitrogen. One reason for keeping the interior of the housing 5 at a reduced pressure or having it filled with an inert gas can be to reduce build-up of contaminants on the optics 6 and/or reduce scattering and absorption of X-ray radiation.

Figure 2:
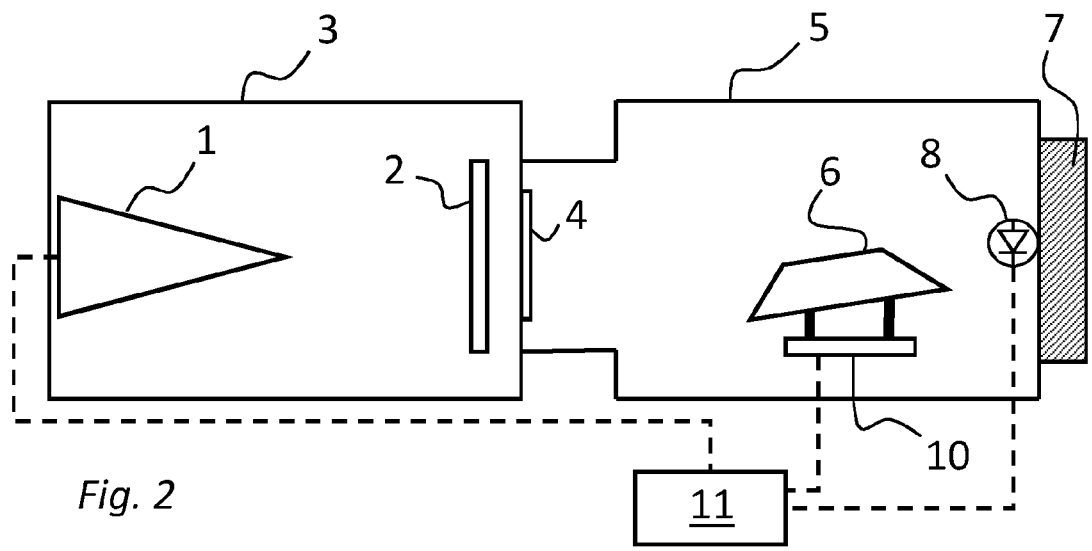
FIG. 2 schematically shows another example of an X-ray system.

Another illustrative implementation is schematically shown in FIG. 2. In this example, the housing 5 is rigidly attached to the enclosure 3. In this implementation alignment may be performed by adjusting either the location of the X-ray spot on the target 2 by moving the electron beam created by the electron source 1, or the position or orientation of the X-ray optics 6 by means of a manipulator 10. Since the housing 5 is connected to the enclosure 3 in a rigid and radiation shielding fashion, no X-ray radiation will be present outside the housing irrespective of how the alignment procedure is performed, as long as the shutter 7 is closed. The electron source 1 may in this implementation comprise suitable electro-optical components such as deflector plates or alignment coils for adjusting the location of the X-ray spot on the target 2. The manipulator 10 may provide for manual or motorized movement of the X-ray optics. Preferably, the manipulator 10 and the X-ray source 1, as well as the detector 8, are connected to a controller 11 for automated alignment (indicated by dashed lines in the figure), such that alignment adjustments can be conveniently made to increase the detector signal. This implementation may provide for a shorter distance between the optics 6 and the X-ray spot on the target 2. The X-ray source 1 is contained in the enclosure 3 and thus there is no need for providing a reduced pressure within the housing 5. The window 4 serves as an interface between the reduced-pressure region inside the enclosure 3 and the housing 5. Since the housing 5 only needs to provide radiation shielding, the construction of the manipulator 10 may be somewhat simplified. The housing 5 may be flushed with an inert gas, such as helium, to reduce air scattering and absorption and also to prevent contamination of the X-ray optics.

Figure 3:
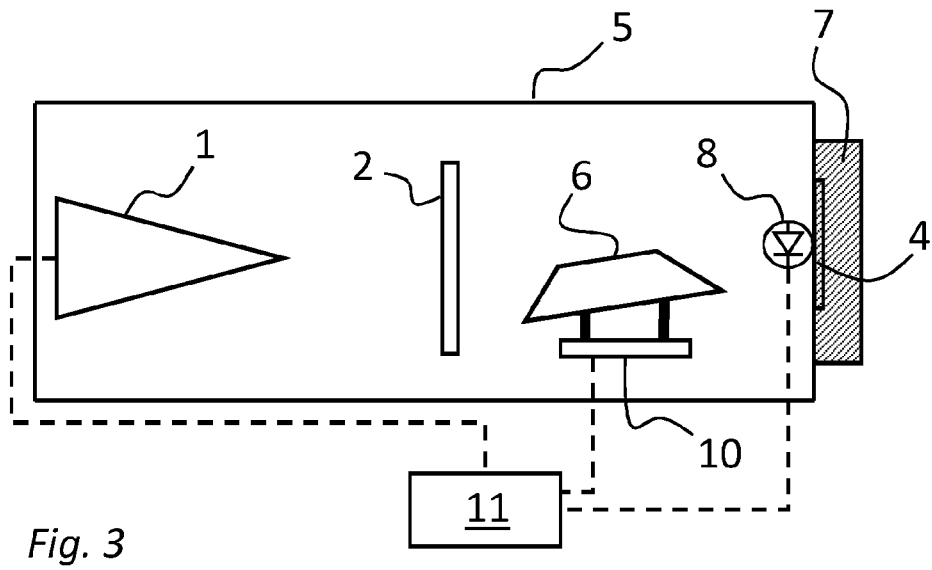
FIG. 3 schematically shows another example of an X-ray system.

Yet another illustrative implementation is schematically shown in FIG. 3. In this implementation, the radiation shielded housing 5 is extended to also comprise the enclosure for the X-ray source 1. The distance between the target 2 (and thus the X-ray spot) and the X-ray optics 6 may then be even further reduced since no X-ray transparent window is needed there between. The reduced-pressure region is in this case provided within the radiation shielded housing 5. Thus, the X-ray transparent window 4 is preferably provided at the outlet port and will thus be covered by the shutter 7 when it is in its closed position. An implementation of the kind shown in FIG. 3 may be useful for an X-ray system designed to provide soft X-ray radiation (energy below about 4 keV). The X-ray source 1, the manipulator 10 for the X-ray optics, and the detector(s) 8 may be connected to the controller 11 in a similar manner as for the implementation of FIG. 2.

Figure 4:
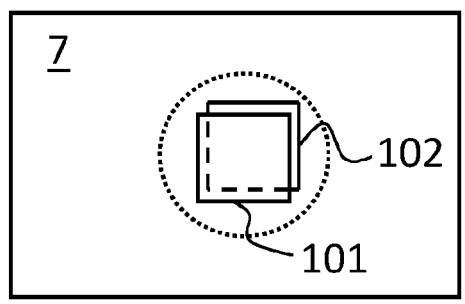
FIG. 4 schematically shows an exemplary detector arrangement.

An exemplary detector arrangement is schematically shown in FIG. 4. A plan view of the shutter 7 is shown, as seen along the X-ray beam path inside the housing 5. The outlet port through which X-ray radiation is emitted from the housing 5 is schematically shown as a dotted circle in FIG. 4. Two diodes 101, 102 are provided on the shutter 7 at a location that will be positioned in front of the outlet port when the shutter is in the closed position. The first diode 101 is placed closest to the X-ray optics and is used for detecting X-ray radiation within the predetermined desired energy range. The second diode 102 is placed behind the first diode as seen in the direction of the emitted X-ray radiation. In FIG. 4, part of the second diode 102 is drawn with dashed lines to illustrate that it is located behind the first diode 101. Thus, the first diode may act as a high pass filter for the second diode. The second diode may then be used to detect whether X-ray radiation with energy outside of the predetermined energy range is emitted from the X-ray optics. An optional filter (not shown in FIG. 4) may be placed between the two diodes if further energy filtering is required.

Generally, embodiments may include one or more electromechanical actuators, motors, or the like for effecting movement of the shutter between its closed and open positions. Such actuators, motors, or the like may be connected to the controller discussed above or may have one or more separate dedicated controllers. In implementations where the position of the shutter is to be controlled based on input from detectors, it is preferred to have the detectors and the actuators/motors connected to a common controller. The X-ray system may be implemented using a single controller, handling all control input and output.

Figure 5:
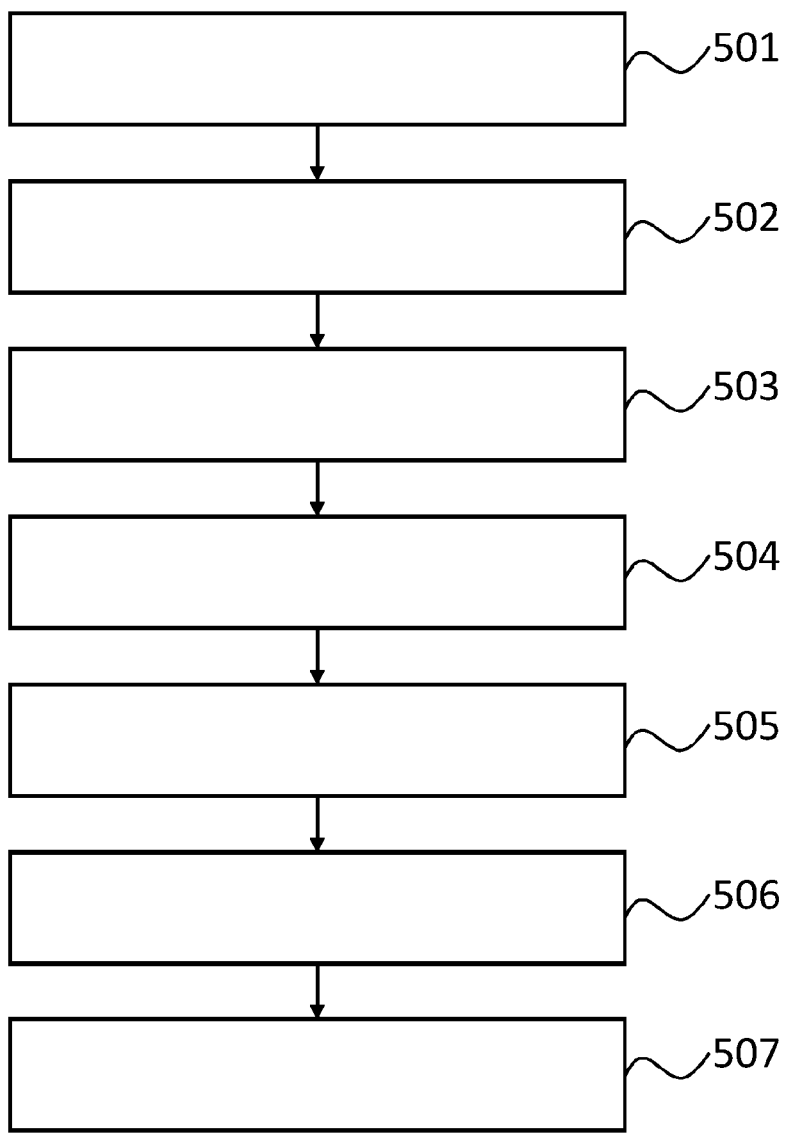
FIG. 5 shows a schematic flow chart of a method according to the invention.

With reference to FIG. 5, an exemplary method of operating an X-ray system according to the invention comprises generating 501 an X-ray beam using an electron-impact X-ray source and directing 502 the X-ray beam into a radiation-shielded housing having an X-ray outlet port. The X-ray beam is directed 503 toward the outlet port using an X-ray optical element that is arranged within the radiation-shielded housing. A shutter arranged at the outlet port is used 504 for allowing or preventing X-ray output through the outlet port, wherein the shutter is moved between an open position at which X-ray output through the outlet port is allowed, and a closed position at which X-ray output through the outlet port is prevented. The method may also include detecting 505 X-ray radiation that is directed towards the outlet port. Optionally the method may include a further step of aligning 506 the relative orientation of the X-ray source spot and the X-ray optics to increase the amount of X-ray radiation emitted through said outlet port. This may be done by adjusting the relative orientation while the shutter is closed, preferably using a controller that is connected to both one or more detectors and alignment manipulators in the X-ray system. The adjustment may be performed such that the detected amount of X-ray radiation directed towards the outlet port is increased. The controller may be configured to stop further adjustment once the achieved increase is below a limit value. Furthermore, the method may comprise a step of ensuring, by means of the controller, that the shutter is closed when the detector detects X-ray radiation with an energy outside of the predetermined range.

In a further embodiment the method comprises adjusting 507 the relative orientation between the X-ray spot and the X-ray optics and/or between the X-ray optics and the outlet port such that the amount of detected X-ray radiation with an energy outside of the predetermined range is below a predetermined threshold. Preferably this adjustment is performed by the controller while the shutter is closed, thus preventing X-ray radiation with energy outside of the predetermined range to be emitted through the outlet port.

CONCLUSION

An X-ray system is disclosed, comprising an electron-impact X-ray source configured to generate an X-ray beam; a radiation-shielded housing having an X-ray outlet port; an X-ray optical element arranged within said radiation-shielded housing configured to direct said X-ray beam toward said outlet port; and a shutter arranged at said outlet port, said shutter being movable between an open position at which X-ray output through the outlet port is allowed, and a closed position at which X-ray output through the outlet port is prevented. In some embodiments, X-ray radiation directed towards the outlet port is detected in order to facilitate alignment of components in the system and/or for safety reasons to prevent inadvertent output of radiation. A corresponding method of operating an X-ray system is also disclosed.

The invention claimed is:

1. An X-ray system comprising
an electron-impact X-ray source configured to generate an X-ray beam;
a radiation-shielded housing having an X-ray outlet port;
an X-ray optical element arranged within said radiation-shielded housing configured to direct said X-ray beam toward said outlet port; and
a shutter arranged at said outlet port, said shutter being movable between an open position at which X-ray output through the outlet port is allowed, and a closed position at which X-ray output through the outlet port is prevented; and
a detector arranged within said radiation-shielded housing and configured to detect X-ray radiation from the X-ray source directed towards said outlet port;
wherein said detector is configured to detect X-ray radiation within a first energy range.

2. The system of claim 1, wherein said detector comprises a filter preventing X-ray radiation with an energy outside of said first energy range from being detected.

3. The system of claim 1, wherein said detector comprises a diode.

4. The system of claim 1, wherein said detector comprises a first detector element for detecting X-ray radiation within said first energy range, and a second detector element for detecting X-ray radiation within a second energy range.

5. The system of claim 1, wherein said X-ray optical element is configured to only transmit X-ray photons within a predetermined energy range.

6. The system of claim 5, wherein said first energy range is selected to fall outside of, particularly above, said predetermined energy range.

7. The system of claim 5, wherein the system is configured to ensure that the shutter is in the closed position if detected photons having an energy outside of said predetermined energy range exceed a predetermined threshold.

8. The system of claim 1, further comprising a controller connected to receive a detector signal from said detector indicative of X-ray radiation within a desired energy range, said controller being arranged to adjust an alignment between said X-ray source and said X-ray optical element and/or between said X-ray optical element and said outlet port such that said detector signal is increased.

9. The system of claim 1, further comprising a manipulator, controllable from outside of the radiation shielded housing, arranged to adjust position and/or orientation of the X-ray optical element.

10. A method of operating an X-ray system, the method comprising:
generating an X-ray beam using an electron-impact X-ray source;
directing the X-ray beam into a radiation-shielded housing having an X-ray outlet port;
directing the X-ray beam toward said outlet port using an X-ray optical element arranged within said radiation-shielded housing;
using a shutter arranged at said outlet port to allow or prevent X-ray output through the outlet port by moving said shutter between an open position at which X-ray output through the outlet port is allowed, and a closed position at which X-ray output through the outlet port is prevented; and
detecting, using a detector arranged within said radiation-shielded housing, X-ray radiation within a first energy range directed towards said outlet port.

11. The method of claim 10, wherein said X-ray optical element is configured to transmit X-ray radiation within a predetermined energy range.

12. The method of claim 11, wherein said first energy range is selected to fall outside of, particularly above, said predetermined energy range.

13. The method of claim 12, further comprising ensuring that the shutter is in said closed position if detected photons having an energy outside of said predetermined energy range exceed a predetermined threshold.

14. The method claim 10, further comprising adjusting an alignment between said X-ray source and said X-ray optical element and/or between said X-ray optical element and said outlet port such that detected X-ray radiation within a desired energy range directed towards the outlet port is increased.

15. The method of claim 13, further comprising adjusting an alignment between the X-ray source and the X-ray optical element and/or an alignment between the X-ray optical element and the outlet port to reduce the detected photons having an energy outside of said predetermined energy range to below said threshold.

* * * * *